United States Patent [19]

Andera et al.

[11] 4,201,319

[45] May 6, 1980

[54] DISPENSING SYSTEM EMPLOYING LIQUID CRYOGEN

[75] Inventors: Joseph F. Andera, Trumbull; Robert C. Eisenberg, Milford, both of Conn.

[73] Assignee: Frigitronics of Conn., Inc., Shelton, Conn.

[21] Appl. No.: 936,816

[22] Filed: Aug. 25, 1978

Related U.S. Application Data

[63] Continuation of Ser. No. 783,967, Apr. 4, 1977, abandoned.

[51] Int. Cl.² .............................................. B65D 83/14
[52] U.S. Cl. ........................... 222/396; 128/DIG. 27; 222/399; 239/302
[58] Field of Search ................... 222/3, 394, 395, 396, 222/399; 228/225, 303.1, 400, DIG. 27; 251/25

[56] References Cited

U.S. PATENT DOCUMENTS

| 2,131,516 | 9/1938 | Leffert et al. | 128/225 |
| 2,589,728 | 3/1952 | Pratt | 128/225 |
| 2,784,712 | 3/1957 | Cassidy | 251/25 X |
| 2,805,037 | 9/1957 | Bruce | 251/25 |
| 3,794,039 | 2/1974 | Kollner et al. | 128/400 |

Primary Examiner—Robert J. Spar
Assistant Examiner—Fred A. Silverberg
Attorney, Agent, or Firm—Parmelee, Johnson, Bollinger & Bramblett

[57] ABSTRACT

A system for dispensing a cryogen such as liquid nitrogen. The system employs two vessels containing the liquid cryogen. One serves as a pressure vessel and the other as a storage vessel. Liquid from the pressure vessel is vaporized in a ballast chamber exposed to ambient temperature, resulting in pressurized refrigerant gas. A valve selectively admits the pressurized gas into the liquid storage vessel, causing the stored liquid to be dispensed at a selected site.

11 Claims, 3 Drawing Figures

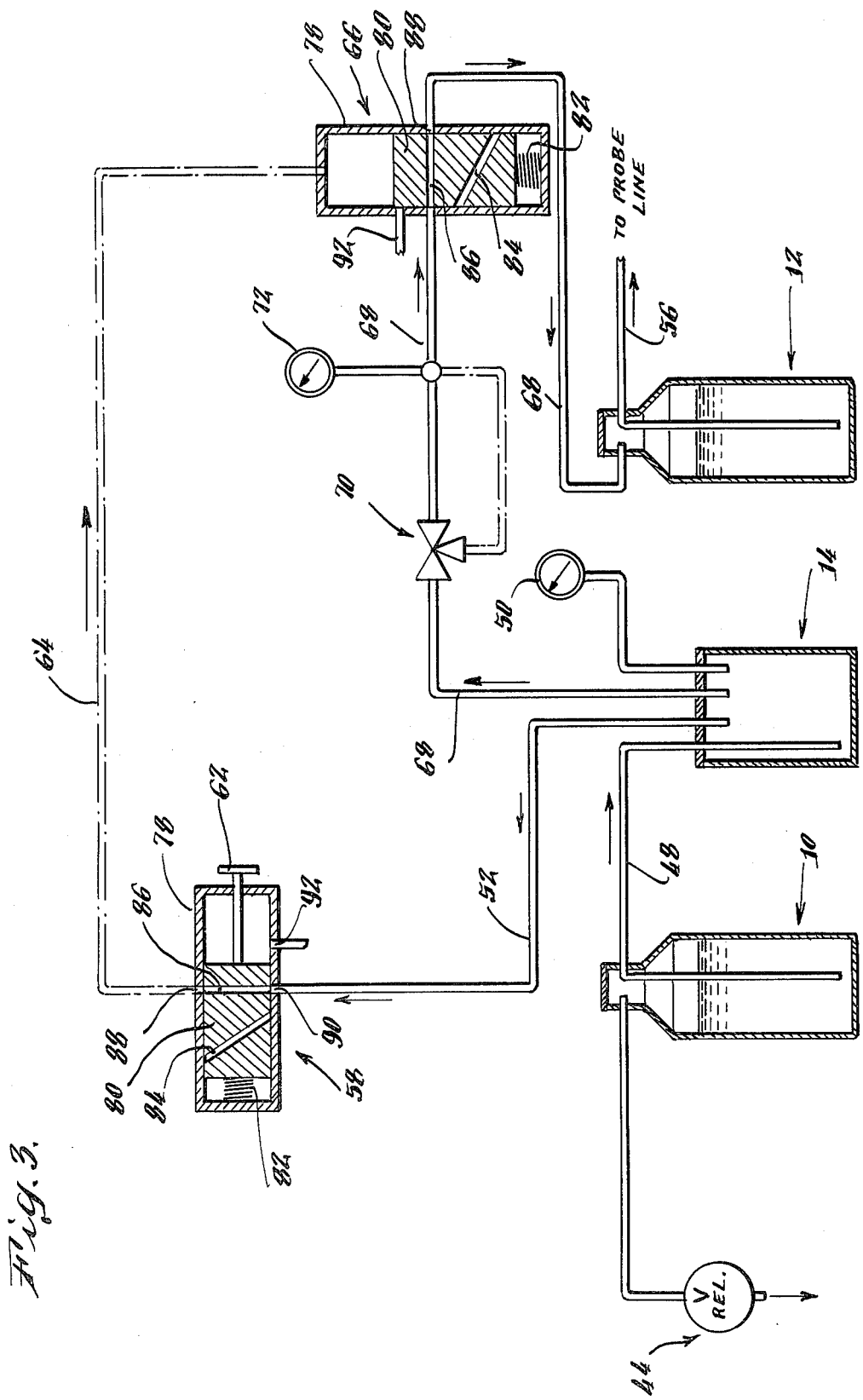

DISPENSING SYSTEM EMPLOYING LIQUID CRYOGEN

This is a continuation of application Ser. No. 783,967 filed Apr. 4, 1977 now abandoned.

BACKGROUND OF THE INVENTION

Liquid nitrogen is commonly used by dermatologists and other medical practitioners for the treatment of various tumors and lesions. Such treatment is well accepted and has been utilized for a number of years. The methods of application vary widely. Some physicians, for example, apply the liquid nitrogen with a cotton swab. Others utilize a more sophisticated approach, using specially designed self-pressurizing flasks such as those shown in U.S. Pat. Nos. 3,702,114 and 3,739,956. The latter method, while effective, is somewhat limited by the relatively small volume of liquid nitrogen which can be contained in the flask. Furthermore, the self-pressurizing nature of the flask means that pressure drops considerably upon use so that sustained dispensing of the liquid nitrogen cannot be achieved.

In many larger liquid nitrogen systems, such as those for use in neurosurgery, the pressure problem has been overcome by the insertion of heaters into the liquid nitrogen containers. This has the obvious disadvantage of requiring an external power supply and also of introducing additional electrical circuitry into the operating room atmosphere. Still another problem encountered with these larger capacity liquid nitrogen systems, is that the valves controlling the liquid nitrogen flow are highly susceptible to freezing and become inoperable.

There are also certain circumstances wherein it would be highly desirable to be able to transport a liquid nitrogen treatment facility into the field. For example, liquid nitrogen has been used quite successfully by veterinarians for the treatment of certain diseases of cattle. To be successfully used for this purpose, the apparatus should be light in weight, of relatively high capacity, and not require any external power supply.

Other features, which are difficult to achieve in prior art systems but are highly desirable, are simple regulation of the liquid nitrogen discharge velocity, accurate control with abrupt termination of liquid nitrogen flow when desired, and a pulsed spray rather than a continuous stream. A pulsed spray reduces dripping of sprayed liquid and improves visibility at the site.

Accordingly, it is a primary object of the present invention to provide a simplified system for dispensing a liquid cryogen. Other objects are to provide such a system: which does not require an electrical power supply; wherein valving is not exposed to liquid cryogen; which has a large capacity of cryogen; which has sustained dispensing ability; which permits either continuous flow or pulsed flow; and which has improved accuracy of control. The manner in which these objects are achieved will become apparent from the following description and appended claims.

SUMMARY OF THE INVENTION

Apparatus for dispensing a liquid which comprises a pressure vessel containing a quantity of a liquid having a boiling point below ambient temperature and a vapor space. A ballast chamber is provided which has its interior in heat transfer relationship with the ambient temperature and is connected to the pressure vessel by means of a transfer conduit which has one end positioned within the pressure vessel below the normal liquid level, and its other end in the ballast chamber. A supply vessel contains a quantity of the liquid to be dispensed and a liquid dispensing line has one end positioned within the supply vessel below the normal liquid level, and its other end at a liquid dispensing site. Means are provided for selectively interconnecting the interior of the ballast chamber with the interior of the supply vessel to pressurize the supply vessel and dispense the liquid therefrom.

BRIEF DESCRIPTION OF THE DRAWINGS

FIG. 3 is an illustration similar to FIG. 2, showing the system in its dispensing mode.

DESCRIPTION OF THE PREFERRED EMBODIMENT

Figure 1:
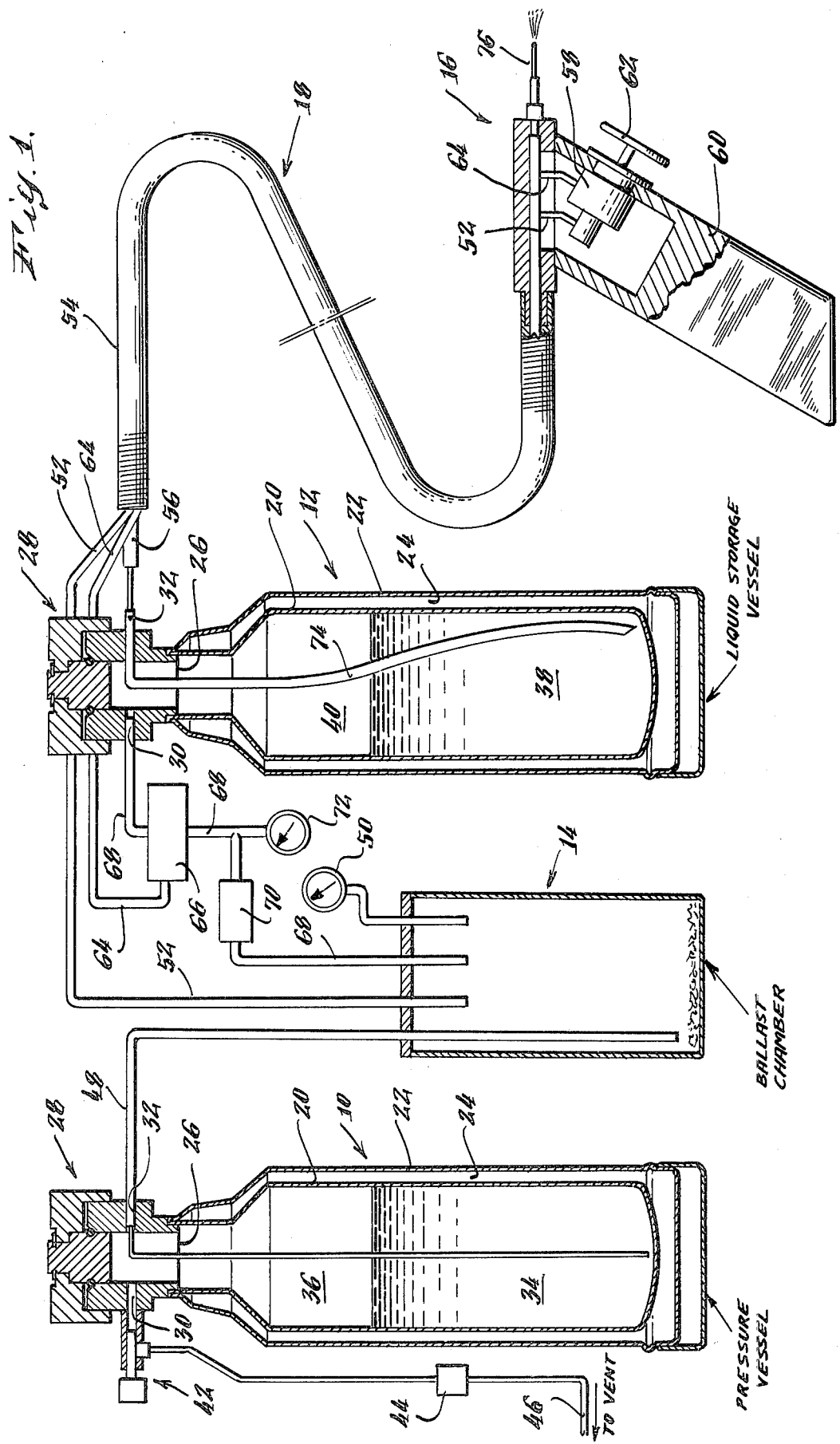
FIG. 1 illustrates a system constructed in accordance with the present invention in partial cross section to illustrate its internal construction.

With particular reference to FIG. 1, there is illustrated a system in accordance with the present invention, comprising a pressure vessel 10 and a liquid storage vessel 12, interconnected through a ballast chamber 14, to supply a liquid utilization device such as cryosurgical spary gun 16 through an insulated delivery line 18. Delivery line 18 may be constructed in any of a variety of ways. One suitable form of construction is disclosed in U.S. Pat. No. 3,907,339. Pressure vessel 10 and storage vessel 12 are substantially identical and, accordingly, similar parts thereof will be assigned similar reference numerals. Each is a conventional Dewar comprising an internal flask 20 and an outer casing 22 defining a vacuum space 24 therebetween. The mouth 26 of each vessel is closed by a conventional cap assembly 28, having an inlet port 30 and outlet port 32. The pressure vessel 10 encloses a cryogenic liquid 34 and a vapor space 36. Similarly, the storage vessel 12 encloses a cryogenic liquid 38 and a vapor space 40. In the described embodiment, the cryogenic liquids 34 and 38, are both liquid nitrogen. However, it is not essential that the same liquid be enclosed in each of the vessels. The inlet port 30 of vessel 10 may be connected through a pressure relief valve 42 to a pressure vent valve 44 and a vent 46.

The ballast chamber 14, which interconnects the vessels 10 and 12, is exposed to the temperature of the ambient atmosphere and is constructed of a material, such as aluminum, having relatively high heat conductivity. A line 48 extends from within the pressure vessel 10 and below the level of the liquid 34, to within the interior of the ballast chamber 14. A pressure gauge 50 permits monitoring of the internal pressure of the chamber 14.

A control line 52 extends from within the ballast chamber 14, and passes between the outer sheath 54 and inner tube 56 of the delivery line 18 to one port of a three-way valve 58 mounted in the pistol grip 60 of spray gun 16, where it may be actuated by a trigger 62. Another line 64 extends from the three-way valve 58, and beneath sheath 54, to the operating port of a piloted three-way main valve 66.

A pressurizing conduit or pressure line 68 extends from the ballast chamber 14 and passes through a pressure regulator 70 and main valve 66, to the inlet port 30 of storage vessel 12. Intermediate the pressure regulator 70 and main valve 66, there is mounted a pressure gauge 72.

A dip tube 74 extends from below the level of the liquid 38 in the storage vessel 12, and connects to the inner tube 56 of the delivery line 18 and into fluid flow communication with a nozzle 76 on spray gun 16. It is to be understood that the system of this invention is not limited to use with a gun for spraying liquid nitrogen. The open nozzle, for example, could be replaced by a cryosurgical probe having suitable means for venting exhaust gas.

OPERATION

The operation of the system of this invention will now be explained, with particular reference to the schematic diagrams of FIGS. 2 and 3. In these diagrams, elements similar to those illustrated in FIG. 1 are given similar reference numerals. In these illustrations, the three-way valves 58, 66, are shown as substantially identical slide valves. Three-way valve 58 is illustrated as including a housing 78 and an inner slide 80 operable by the trigger 62 against the force of a spring 82. The inner slide 80 defines a pair of passages 84, 86, which are alignable with ports 88, 90, 92 in the housing 78. Main valve 66 is similarly constructed and the parts are given similar reference numerals. The primary distinction between valves 66 and 58 is that main valve 66 is operated pneumatically within the housing 78 by pressure exerted through line 64.

Figure 2:
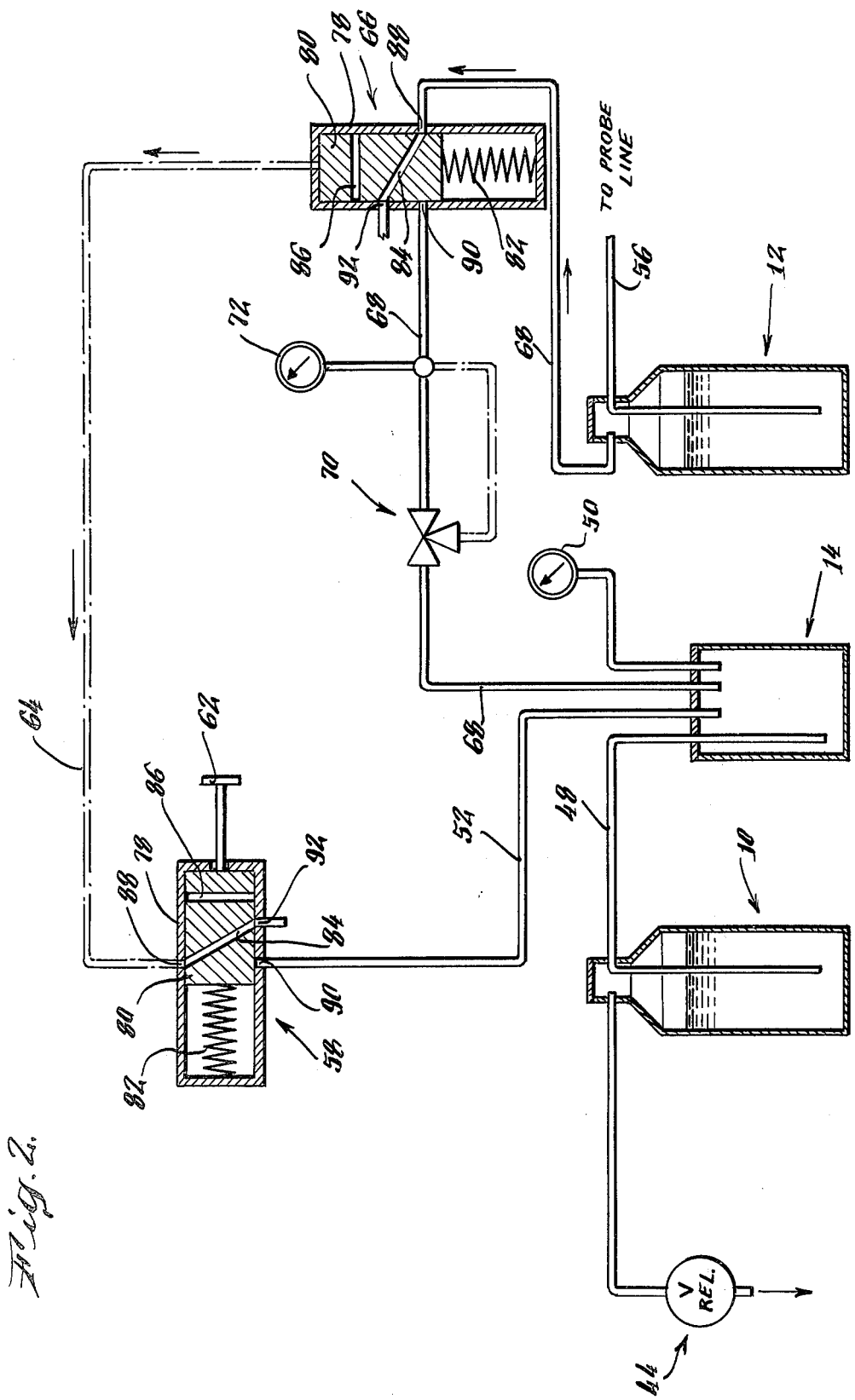
FIG. 2 is a schematic diagram of the system of FIG. 1 showing the system in its static mode.

FIG. 2 illustrates the system of this invention in its static condition. In this condition liquid nitrogen exists in the pressure vessel 10, the vapor space above the liquid being filled with nitrogen gas. Nitrogen gas alone exists within the ballast chamber 14, which is at ambient atmospheric temperature considerably above the boiling point of liquid nitrogen. The control line 52 and the pressure line 68 are both snubbed off by the respective three-way valves 58, 66 and, accordingly, the pressures within the pressure vessel 10 and the ballast chamber 14 are equalized. The liquid storage vessel 12 also contains liquid nitrogen, but the vapor space above the liquid is vented to atmosphere through pressure line 68 and passage 84 of main valve 66.

In order to dispense liquid nitrogen from the system, the trigger 62 is pressed, causing actuation of three-way valve 58 to the condition illustrated in FIG. 3. The reservoir of pressurized gas within the ballast chamber 14 is now connected through the passage 86 of valve 58 and through line 64 to main valve 66, which is thereby actuated to the illustrated position. In this position, the gas within the ballast chamber 14 is also supplied through the pressure regulator 70, and the passage 86 of main valve 66 to the vapor space within the liquid storage vessel 12. The increased pressure causes liquid nitrogen to be forced outwardly through tube 56 to the spray nozzle or other device. The pressure within ballast chamber 14 is self-replenishing. As the gas pressure therein is released, the imbalance in the pressures within pressure vessel 10 and chamber 14 causes additional liquid nitrogen to pass into the chamber 14 via line 48. This liquid nitrogen immediately flash vaporizes upon entering the chamber 14 thereby continually replenishing the pressure as required. Upon release of the trigger 62, the valves 58, 66, return to the positions illustrated in FIG. 2. This immediately vents the storage vessel 12 to atmosphere through passage 84 of main valve 66, thereby immediately terminating the flow of liquid nitrogen.

The pressure regulator 70 serves an important function in permitting sustained pulsating flow of cryogen from a spray nozzle. This is a valuable feature as it prevents liquid dripping or running from the operative site and also provides better visibility of the site. The pulsing is caused by the formation of bubbles of gas in the cryogenic liquid due to heat absorbed as it flows through the delivery line 18. A higher flow rate exceeds the heat transfer capability of the delivery line insulation, resulting in a continuous liquid stream being ejected. A lower flow rate would result in vaporization of a greater quantity of cryogen with increased gas and decreased liquid delivery. The pressure regulator 70 permits the liquid flow to be precisely matched to the heat transfer through the delivery line 18 for optimal pulsing action.

It is believed that the many advantages of this invention will now be apparent to those skilled in the art. One such advantage is that no valve throughout the system is exposed to liquid nitrogen, thus obviating the freeze-up problem encountered in many prior art designs. Furthermore, the system operates completely without any electrical power requirement, thereby increasing its safety and making it practical for portable field work.

In the foregoing description, the system has been described as operable with liquid nitrogen. However, it will be understood that other fluids may be employed. In fact, two different liquids may be utilized, a low boiling (below ambient) temperature fluid within the pressure vessel 10 for providing the motive force, and any other desired liquid within the storage vessel 12 which is to be dispensed. Also, the ballast chamber has been described as a relatively large volume chamber. Other configurations such as, for example, a coiled metal tube could be utilized. Furthermore, the system is not limited to medical or surgical applications, but may have other uses as well. Accordingly, it will be understood that various modifications may be made in this invention without departing from its spirit and scope. This invention is limited only by the scope of the following claims.

We claim:

1. A system for dispensing a liquid which comprises: a pressure vessel; a pressurizing liquid having a boiling point below ambient temperature contained within said pressure vessel and defining a vapor space thereabove; a ballast chamber having its interior in heat transfer relationship with the ambient atmosphere; a transfer conduit having a first end positioned within said pressure vessel below the normal level of pressurizing liquid therein and a second end positioned in said ballast chamber; a supply vessel containing therein a quantity of liquid to be dispensed; a liquid dispensing line having a first end positioned within said supply vessel below the normal level of liquid therein and a second, discharge, end at a liquid utilizatioon device; and means for selectively interconnecting the interior of said ballast chamber with the interior of said supply vessel to pressurize said supply vessel and dispense said liquid therefrom.

2. The system of claim 1 wherein said pressurizing liquid is liquid nitrogen.

3. The system of claim 1 wherein said liquid to be dispensed is liquid nitrogen.

4. The system of claim 3 wherein said pressurizing liquid is liquid nitrogen.

5. The system of claim 1 wherein said interconnecting means comprises a pressure regulator for maintaining a preselected pressure within said supply vessel.

6. The system of claim 1 wherein said selective interconnecting means comprises: a pressurizing conduit between said ballast chamber and said supply vessel; and means for selectively opening and closing said pressurizing conduit to fluid flow.

7. The system of claim 6 wherein said pressurizing conduit includes a pressure regulator for maintaining a preselected pressure within said supply vessel.

8. The system of claim 7 wherein said opening and closing means comprises: a main valve in said pressurizing conduit; and means for remotely actuating said main valve.

9. The system of claim 8 wherein said remote acutating means comprises: a pilot valve; and a control line connected between said ballast chamber and said main valve through said pilot valve.

10. The system of claim 9 wherein said utilization device is a cryosurgical instrument and said pilot valve is mounted on said instrument.

11. The system of claim 10 wherein said pressurizing and dispensed liquids are liquid nitrogen.

* * * * *